(12) United States Patent
Keating

(10) Patent No.: US 9,339,426 B2
(45) Date of Patent: May 17, 2016

(54) PORTABLE AND DISPOSABLE APPARATUS FOR URINARY ELIMINATION

(71) Applicant: Kathryn Barr Keating, Stratham, NH (US)

(72) Inventor: Kathryn Barr Keating, Stratham, NH (US)

(*) Notice: Subject to any disclaimer, the term of this patent is extended or adjusted under 35 U.S.C. 154(b) by 97 days.

(21) Appl. No.: 13/964,475

(22) Filed: Aug. 12, 2013

(65) Prior Publication Data

US 2014/0303584 A1    Oct. 9, 2014

Related U.S. Application Data

(60) Provisional application No. 61/810,151, filed on Apr. 9, 2013.

(51) Int. Cl.

| | |
|---|---|
| *A61F 13/15* | (2006.01) |
| *A61F 5/44* | (2006.01) |
| *A47K 3/26* | (2006.01) |
| *A61F 13/84* | (2006.01) |
| *A61G 9/00* | (2006.01) |
| *A47K 13/06* | (2006.01) |

(52) U.S. Cl.
CPC ............... *A61F 13/84* (2013.01); *A61G 9/006* (2013.01); *A47K 13/06* (2013.01); *A61F 13/8405* (2013.01); *A61F 2013/8402* (2013.01)

(58) Field of Classification Search
CPC ....... A47K 11/06; A47K 11/00; A47K 13/06; A47K 13/8402; A47K 13/8405
USPC .......................... 604/349, 385.06; 4/449, 443
See application file for complete search history.

(56) References Cited

U.S. PATENT DOCUMENTS

| | | | | |
|---|---|---|---|---|
| 4,996,727 | A * | 3/1991 | Wyatt | 4/484 |
| 6,505,354 | B1 * | 1/2003 | Almonte | 4/144.1 |
| 2004/0216220 | A1 * | 11/2004 | Ernest et al. | 4/144.1 |
| 2009/0036848 | A1 * | 2/2009 | Faiola | 604/329 |

* cited by examiner

*Primary Examiner* — Jacqueline Stephens

(57) ABSTRACT

Portable and disposable apparatus for urinal elimination includes a container with a hydrophilic layer, absorbent fragrance materials, and liquid absorbency materials. The hydrophilic layer, the absorbent fragrance materials, and the liquid absorbency materials absorb all of the urine within the container without any after spillage. Users can use a lid, which is permanently connected with the container from one end, as a privacy shield during urinal elimination process. Once the users are finished with the urinal elimination process, the users can reseal the lid back onto the container so that the container can be disposed at users' convenience.

17 Claims, 10 Drawing Sheets

PORTABLE AND DISPOSABLE APPARATUS FOR URINARY ELIMINATION

The current application claims a priority to the U.S. Provisional Patent application Ser. No. 61/810,151 filed on Apr. 9, 2013.

FIELD OF THE INVENTION

The present invention relates generally to an apparatus and a method for a one time disposable bladder elimination solution. More specifically, the present invention is an apparatus and a method for a convenient, portable, immediate, and disposable bladder elimination solution.

BACKGROUND OF THE INVENTION

Parents often encounter problems finding a bathroom for their kids when they are out from their houses. Even if they are able to find a public bathroom, most of the public bathrooms can be messy and unsanitary due to the number of users. Even though this is a common problem for parents with kids, this can also be a problem for any adults. Currently, there are many different types of disposable bladder elimination products on the market that provides a solution for urinal elimination. However, they are not as portable, convenient, or easy to use. Moreover, the functionality is improved with the packaging and different sizes as well as the material.

It is therefore an object of the present invention to introduce a new apparatus and a method for a portable and disposable product used specifically for one-time urinary bladder elimination so that the messy and unsanitary bathrooms can be avoided. The present invention also provides a privacy shield for the user during the urinal elimination.

DETAIL DESCRIPTIONS OF THE INVENTION

Figure 1:
FIG. 1 is a top perspective view of the present invention.

All illustrations of the drawings are for the purpose of describing selected versions of the present invention and are not intended to limit the scope of the present invention.

The present invention is a portable and disposable apparatus for urinary elimination which comprises a container 1, a hydrophilic layer 2, absorbent fragrance materials 3, liquid absorbency materials 4, a lid 5, and at least one pack of wipe 6. The present invention is used specifically for one-time urinary elimination, where the present invention provides a fast, easy, and clean solution for immediate bathroom use. As shown in FIG. 1-FIG. 4, the hydrophilic layer 2, the absorbent fragrance materials 3, and the liquid absorbency materials 4 are positioned within the container 1. The lid 5 is positioned atop the container 1, sealing the inner components of the present invention.

Figure 5:
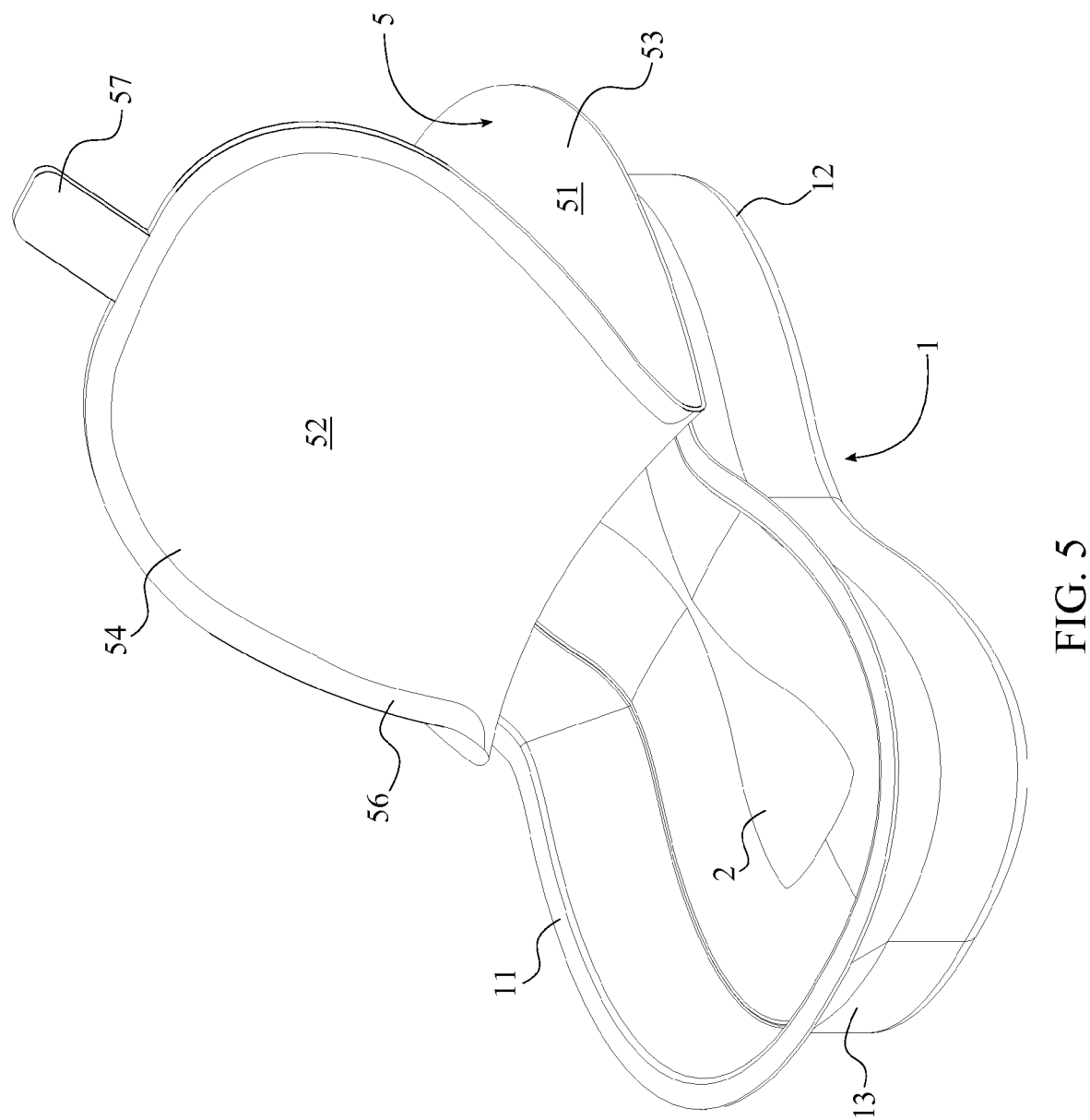
FIG. 5 is a perspective view of the present invention, wherein the lid of the present invention being opened.
Figure 6:
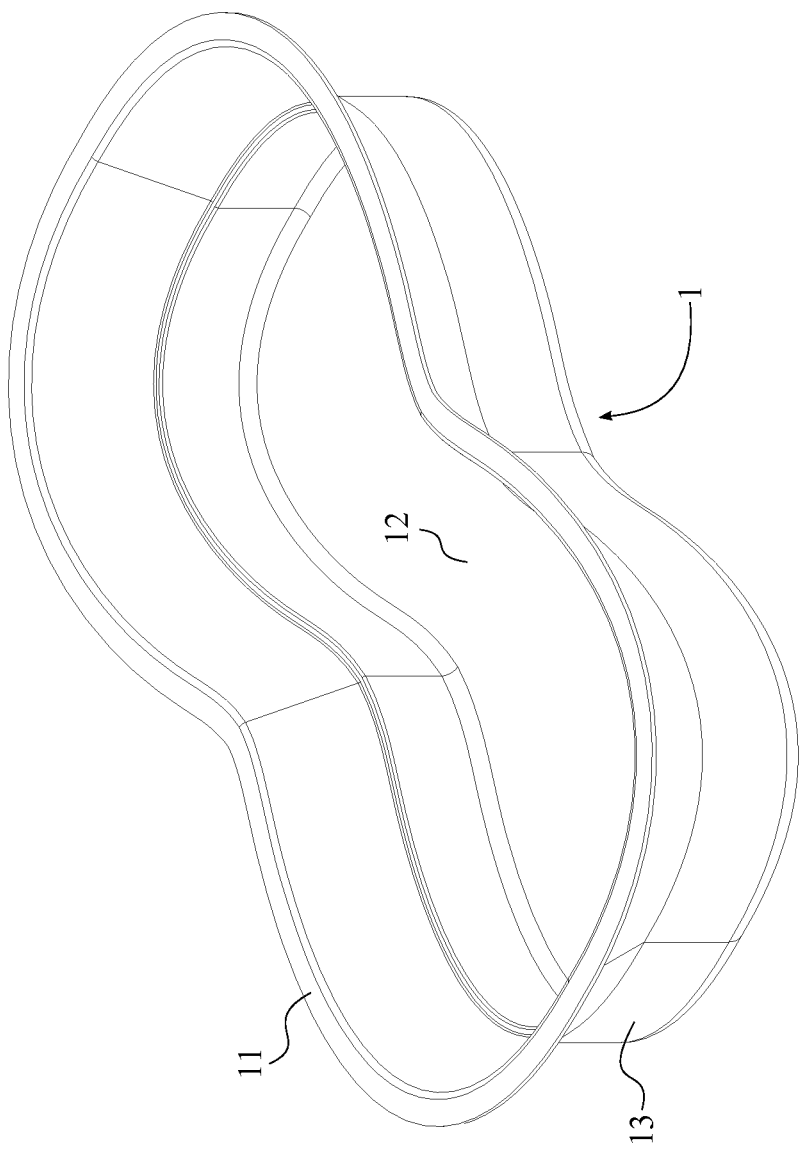
FIG. 6 is a perspective view of the container of the present invention.
Figure 7:
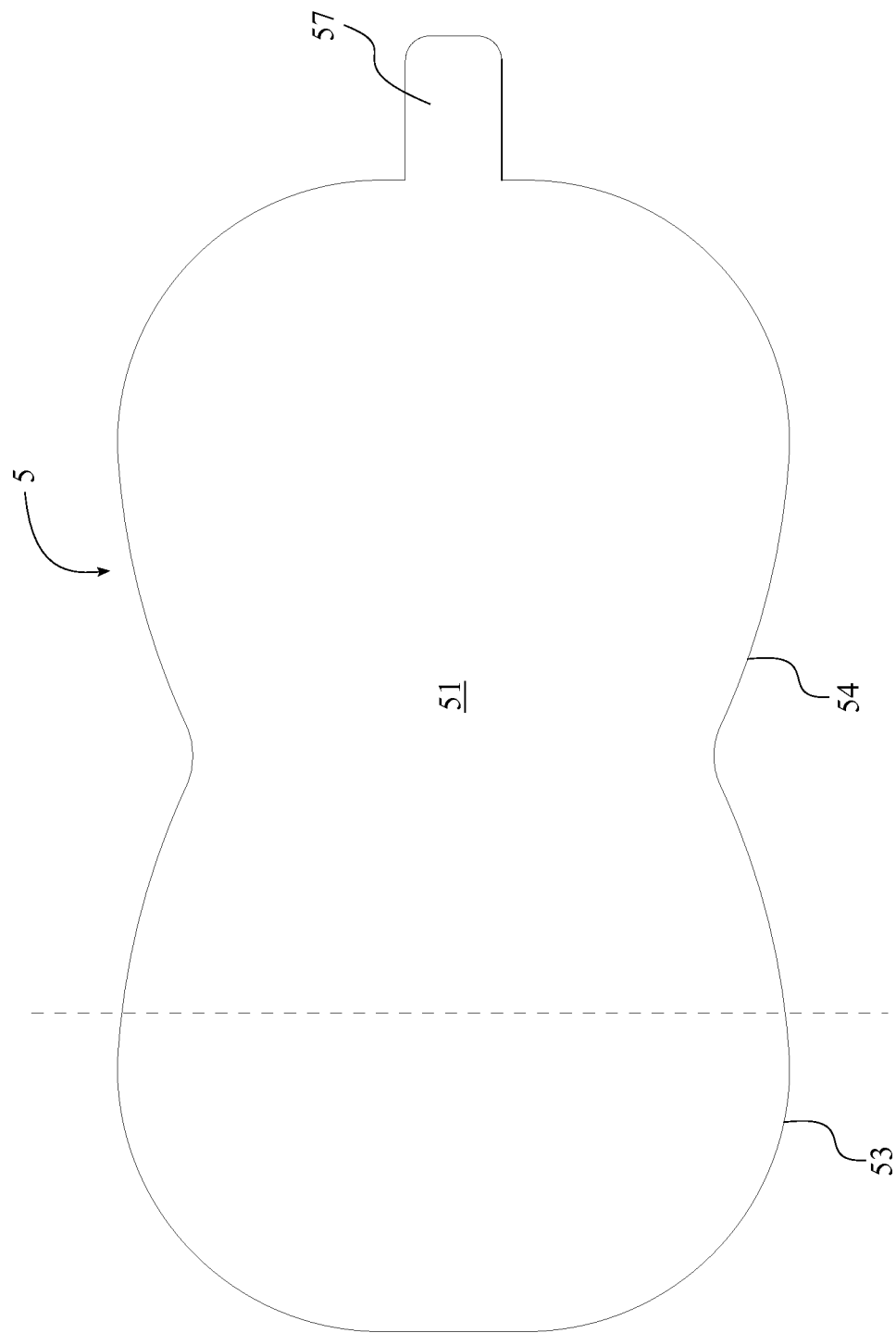
FIG. 7 is a top view of the lid of the present invention, wherein the dash line separates the sealed section and the resealable section.
Figure 8:
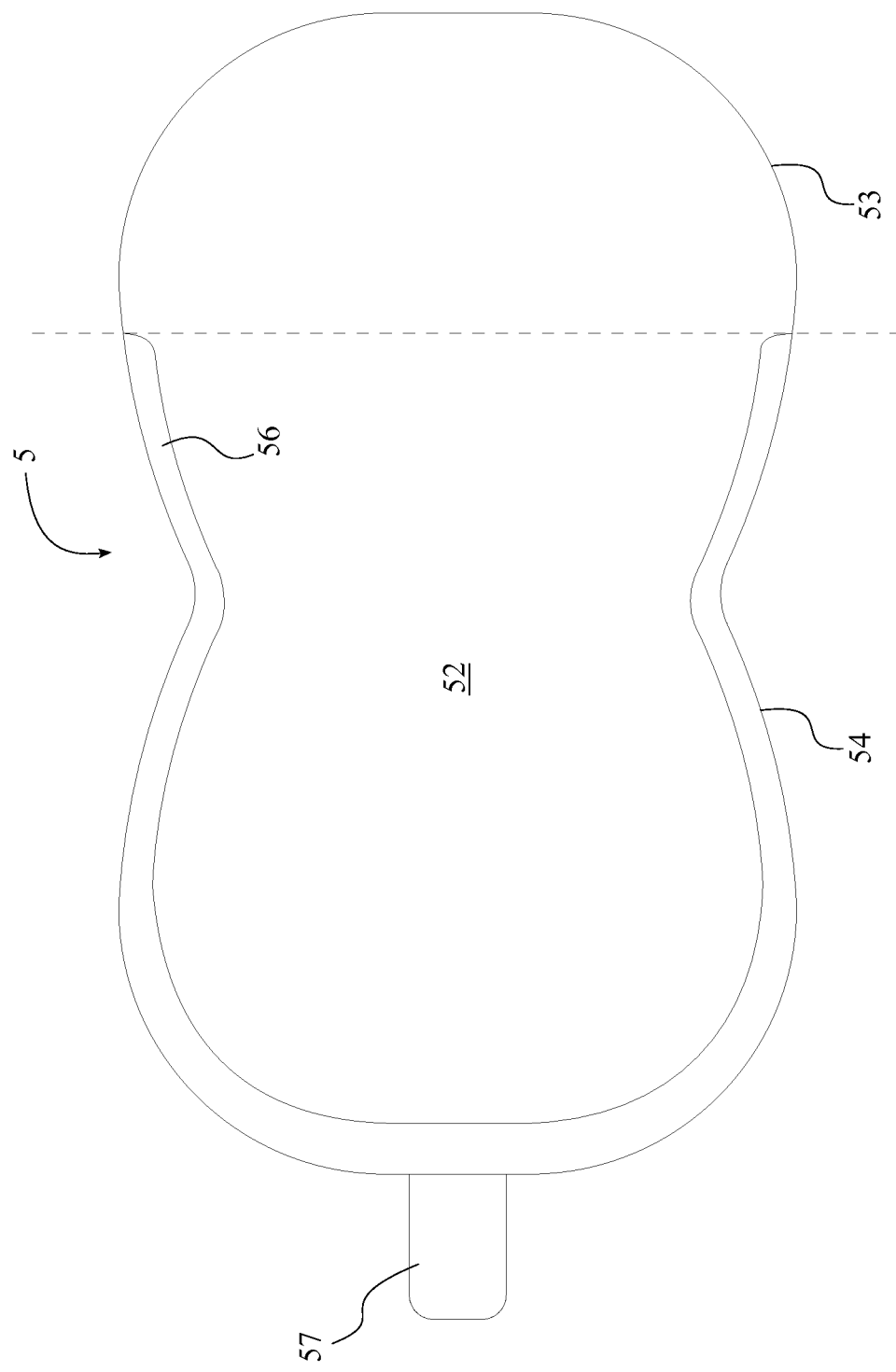
FIG. 8 is a bottom view of the lid of the present invention, wherein the dash line separates the sealed section and the resealable section.
Figure 9:
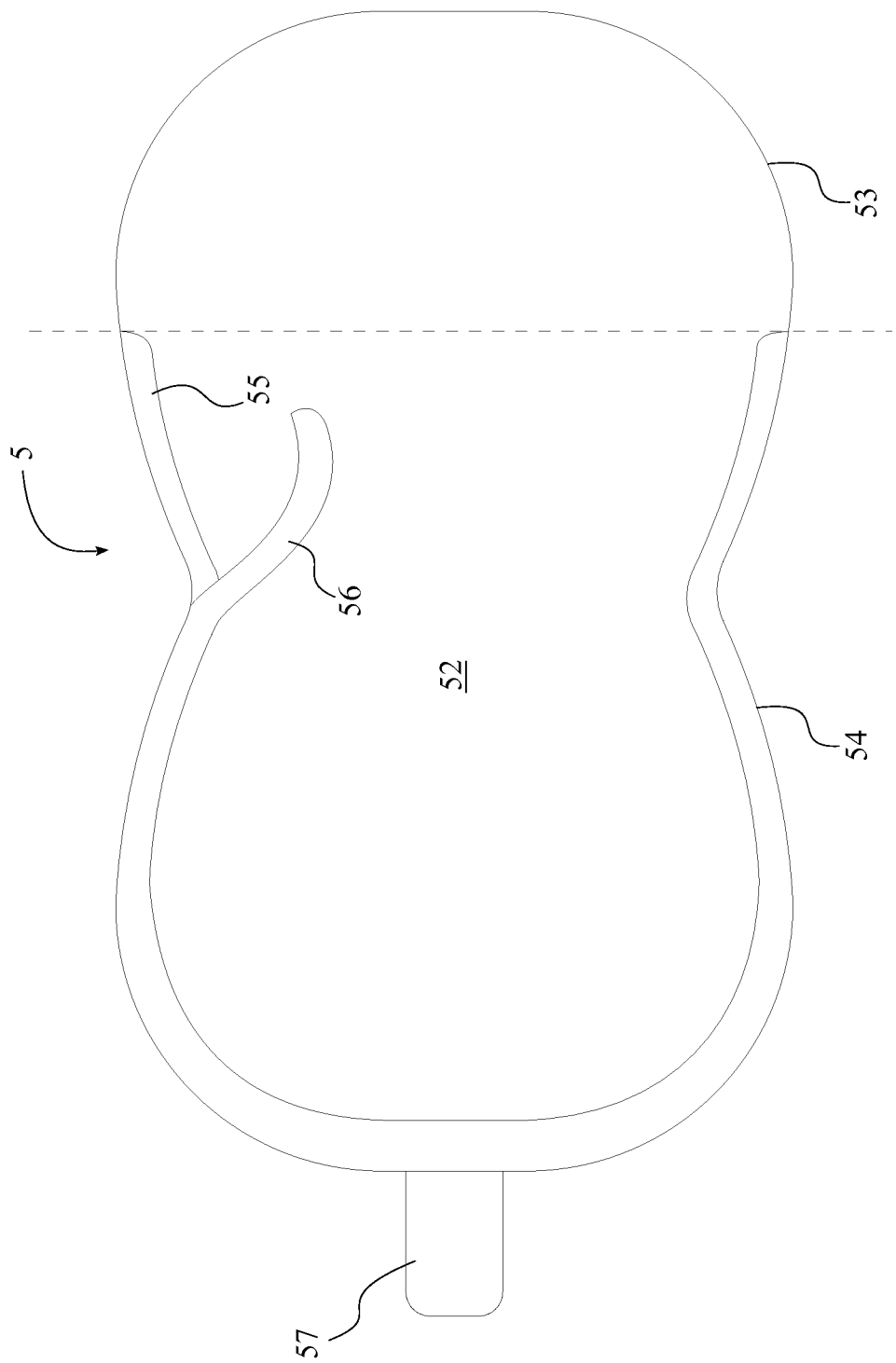
FIG. 9 is a bottom view of the lid of the present invention illustrating the removable film and the adhesive strip, wherein the dash line separates the sealed section and the resealable section.

In reference to FIG. 5 and FIG. 6, the container 1 comprises an outer lip 11, a bottom wall 12, and a lateral wall 13. The lateral wall 13 is perimetrically positioned around the bottom wall 12 in such way that the lateral wall 13 is extended above the bottom wall 12. The outer lip 11 is perimetrically positioned around the lateral wall 13, where the outer lip 11 is positioned parallel with the bottom wall 12 and extended away from the lateral wall 13. The outer lip 11, the bottom wall 12, and the lateral wall 13 complete the container 1 of the present invention where the shape of the container 1 can include, but is not limited to, any geometric or organic shapes as long as the container 1 is able to comfortably fit under the urethral opening of the user for urine discharge. The container 1 is made from any other kind of light weight materials include, but is not limited to, plastic, biodegradable plastic, or polyethylene-coated liquid packaging board.

Figure 4:
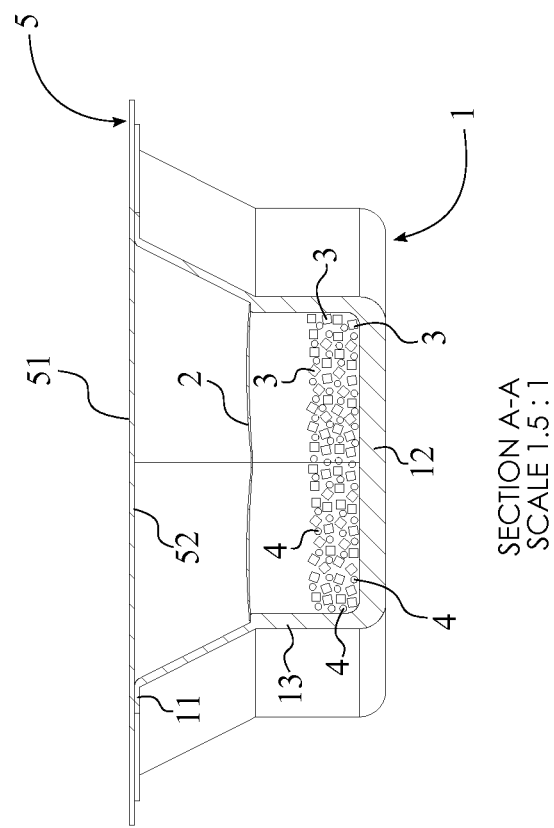
FIG. 4 is a cross section view thereof taken along line A-A of FIG. 3.

In reference to FIG. 4 and FIG. 5, the absorbent fragrance materials 3 and the liquid absorbency materials 4 are adjacently positioned with the bottom wall 12 and the lateral wall 13. The liquid absorbency materials 4 of the present invention include, but are not limited to, sodium polyacrylate, super absorbent polymer, or any other kind of materials that has the ability to absorb higher mass of liquid compare to the mass of the liquid absorbency materials 4. The absorbent fragrance materials 3 of the present invention include, but are not limited to, citrus scented absorbent polymer or any other materials that can absorb and retain extremely large amount of liquid relative to their own mass while providing a pleasant scent. The present invention further comprises antimicrobial agents in order to prevent, destroy, or migrating of any kind of pests, where the antimicrobial agents can be petroleum distillates or any other similar ingredients. The hydrophilic layer 2 is perimetrically connected to the lateral wall 13 in such way that the hydrophilic layer 2 is positioned in between the bottom wall 12 and the outer lip 11. Moreover, the hydrophilic layer 2 is positioned atop the absorbent fragrance materials 3 and the liquid absorbency materials 4. The hydrophilic layer 2 is made from any hydrophilic materials, such as non woven polypropylene fabric and polyester fabric.

In reference to FIG. 5, FIG. 7, FIG. 8, and FIG. 9, the lid 5 comprises a top face 51, a bottom face 52, a sealed section 53, a resealable section 54, an adhesive strip 55, a removable film 56, and a tab 57. The top face 51 and the bottom face 52 are oppositely positioned from each other on the lid 5, where the top face 51 is directed toward the user of the present invention and the bottom face 52 is directed toward the inside of the container 1. The top face 51 provides space so that product information can be printed on the top face 51, where the product information can be ingredient information, basic instructions for proper usage, product description, product logo, and decorative elements. The sealed section 53 and the resealable section 54 are adjacently positioned with each other on the lid 5. The adhesive strip 55 is perimetrically positioned around the resealable section 54, where the adhesive strip 55 is adjacently positioned with the bottom face 52.

The removable film 56 is perimetrically attached around the adhesive strip 55 and oppositely positioned from the bottom face 52. When the lid 5 is positioned atop the container 1, the sealed section 53 is permanently connected with the outer lip 11 while the resealable section 54 is attached with the outer lip 11 through the removable film 56 in such way that the removable film 56 is positioned in between the adhesive strip 55 and the outer lip 11. The tab 57 is connected to the resealable section 54 and extended outward, where the tab 57 is oppositely positioned from the sealed section 53.

Figure 2:
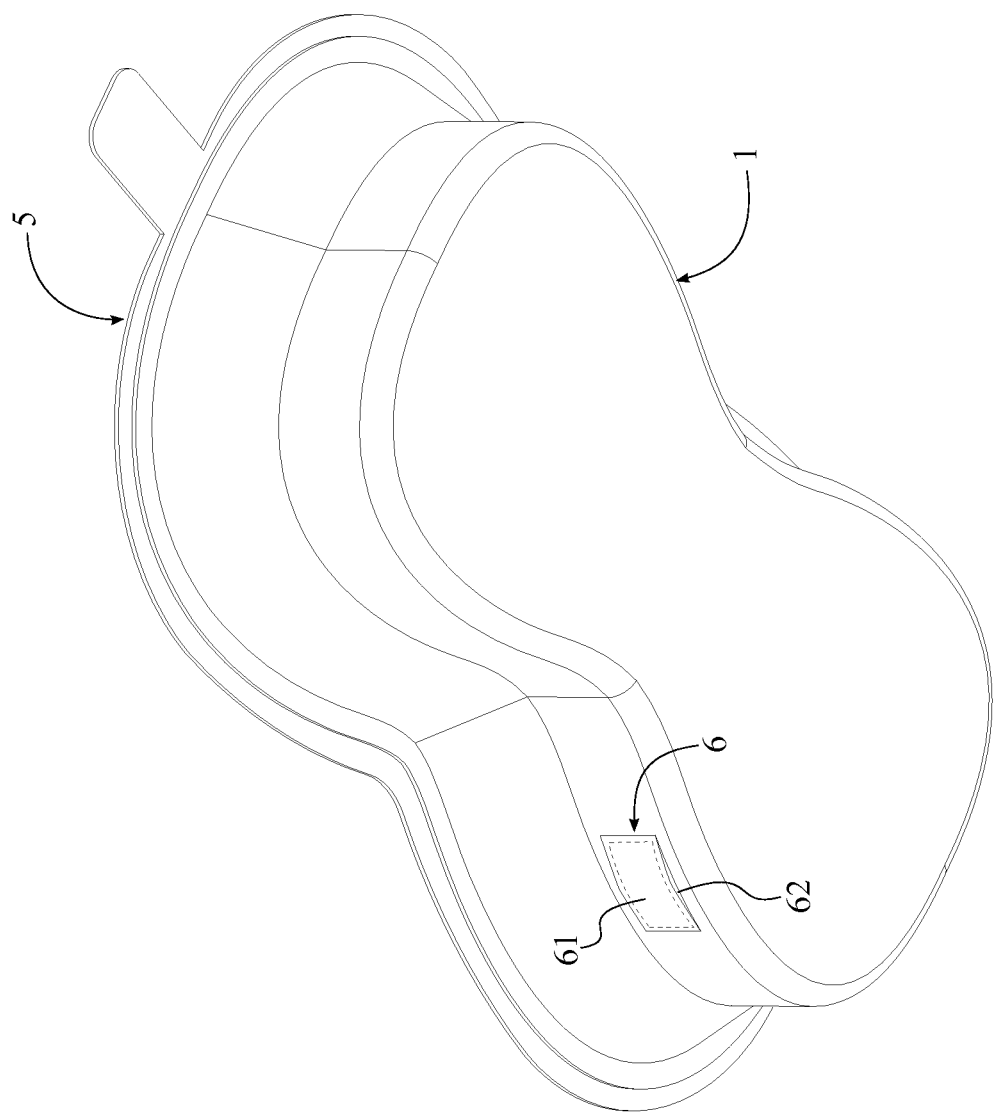
FIG. 2 is a bottom perspective view of the present invention, wherein the dash line illustrates the cleaning wipe of the present invention.
Figure 3:
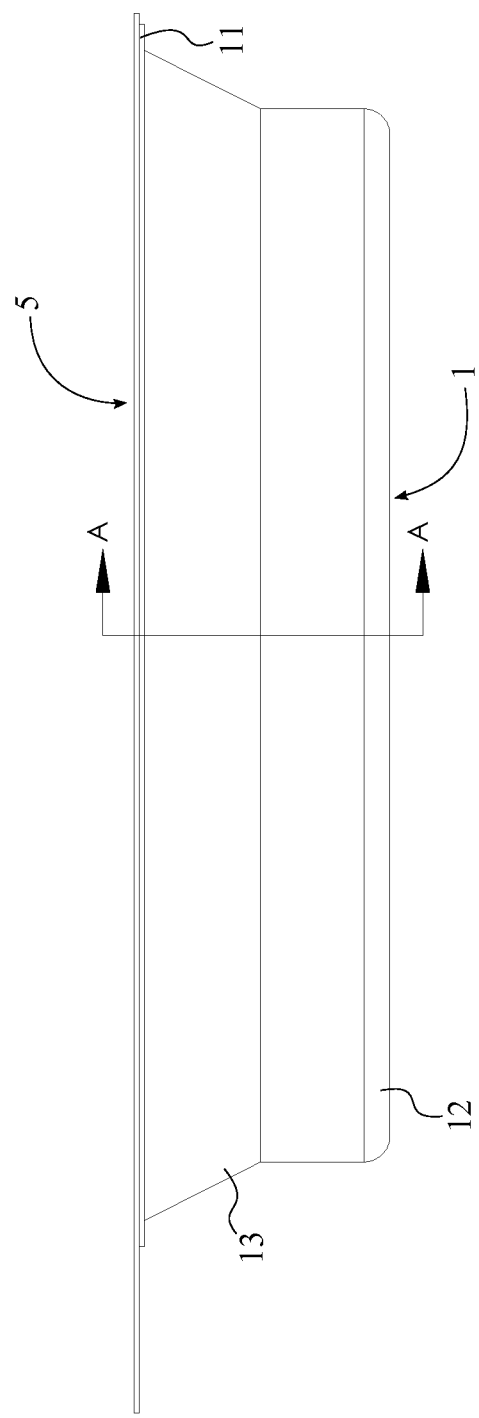
FIG. 3 is a side view of the present invention, showing the plane upon which a cross sectional view is taken shown in FIG. 4.

In reference to FIG. 2, the at least one pack of wipe 6 is attached on to the container 1 and comprises a cleaning wipe 61 and wrapper 62. The cleaning wipe 61 is enclosed by the wrapper 62 so that the user of the present invention is able to receive clean and fresh cleaning wipe 61 from the at least one pack of wipe 6. The cleaning wipe 61 is use for personal hygiene of the user and may moisten with cleaning alcohol. Even though one pack of wipe 6 is used within the present invention, the present invention can also have multiple packs of wipe 6.

Figure 10:
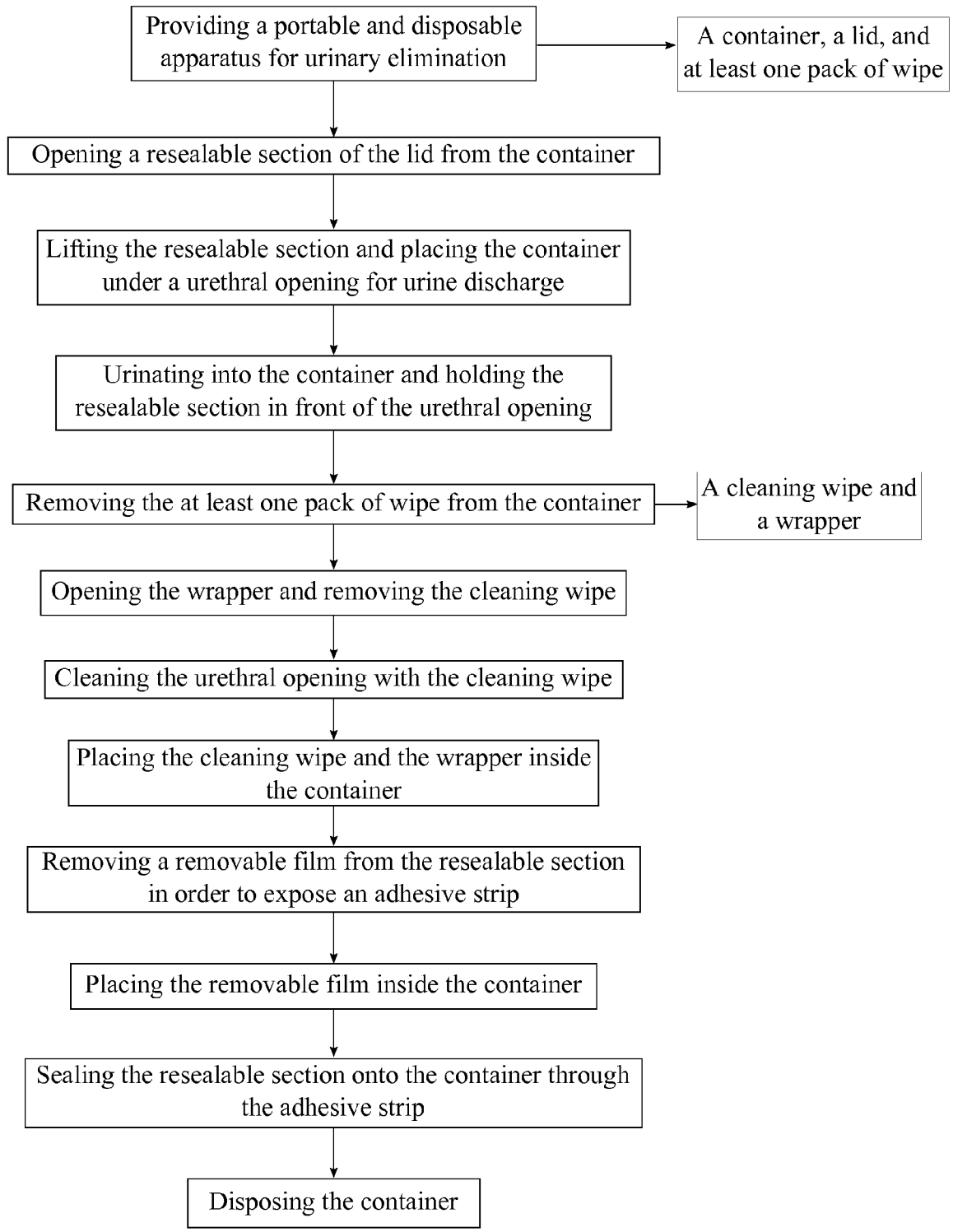
FIG. 10 is a basic flow chart illustrating the method of using the present invention.

In reference to FIG. 10, the method of using the present invention, the user needs to completely open the resealable section 54 away from the container 1. Once the resealable section 54 is opened, the inside of the container 1 is exposed to the user. Then the user lifts the resealable section 54 and places the container 1 under the urethral opening for urine discharge. The user can then urinate into the container 1 while holding the resealable section 54 in front of the urethral opening, where the resealable section 54 functions as a privacy shield to the urethral opening and as a splash guard to the container 1. Once the urine enters into the container 1, the absorbent fragrance materials 3 and the liquid absorbency materials 4 solidify the urine into a dry gel within minutes. Once the user is done urinating into the container 1, the user can remove the at least one pack of wipe 6 from the container 1. Then the user is able to open the wrapper 62 and remove the cleaning wipe 61 from the wrapper 62. The cleaning wipe 61 is then used by the user to clean the urethral opening for sanitary purposes. Then the cleaning wipe 61 and the wrapper 62 are placed within the container 1. Then the user has to remove the removable film 56 from the resealable section 54 so that the adhesive strip 55 can be exposed. Then the removable film 56 is placed within the container 1, and the resealable section 54 is sealed onto the outer lip 11 of the container 1. The adhesive strip 55 provides a tight seal within the resealable section 54 and the outer lip 11 so that the inside debris do not leak out from the present invention. After the container 1 is fully sealed with the resealable section 54, the user can dispose the container 1 at his or her next convenient opportunity.

The present invention can be made into an adult size and a toddler size so that adults and toddlers can have two different sizes. Since the amount of urine discharged from an adult is relatively higher than the amount of urine discharged from a toddler, the amounts of the liquid absorbency materials 4 and the absorbent fragrance materials 3 in the adult size are higher than the toddler size. The container 1 of the adult size is also larger than the container 1 of the toddler size so that each of the containers 1 is able to store the respective amounts of the liquid absorbency materials 4, the absorbent fragrance materials 3, and the discharged urine.

A preferred embodiment of the present invention is made into an hourglass shape in order to provide optimal coverage for the urine discharge, where the hourglass shape provides a perfect placement for the preferred embodiment with respect to the user. The preferred embodiment comprises a perimetrically positioned ledge within the lateral wall 13, where the ledge creates a specific attachment surface for the hydrophilic layer 2 within the container 1. The preferred embodiment uses the super absorbent polymer as the liquid absorbency materials 4, the citrus scented absorbent polymer as the absorbent fragrance materials 3, and the petroleum distillates as the antimicrobial agents. The pack of wipe 6 of the preferred embodiment is located on the lateral wall 13 of the container 1, but can also locate on the bottom wall 12.

Although the invention has been explained in relation to its preferred embodiment, it is to be understood that many other possible modifications and variations can be made without departing from the spirit and scope of the invention as hereinafter claimed.

What is claimed is:

1. A portable and disposable apparatus for urinary elimination comprises:
    a container;
    a hydrophilic layer;
    absorbent fragrance materials;
    liquid absorbency materials;
    a lid;
    at least one pack of wipe;
    the container comprises an outer lip, a bottom wall, and a lateral wall;
    the lid comprises a top face, a bottom face, a sealed section, a resealable section, an adhesive strip, a removable film, and a tab;
    the hydrophilic layer, the absorbency fragrance materials, the liquid absorbency materials being positioned within the container;
    the lid being positioned atop the container;
    the sealed section being permanently connected with the outer lip;
    the resealable section being attached with the outer lip through the removable film; and
    the removable film being positioned in between the adhesive strip and the outer lip.

2. The portable and disposable apparatus for urinary elimination as claimed in claim 1 comprises:
    the lateral wall being perimetrically positioned around the bottom wall;
    the lateral wall being extended above the bottom wall;
    the outer lip being perimetrically positioned around the lateral wall; and
    the outer lip being positioned parallel with the bottom wall and extended away from the bottom wall.

3. The portable and disposable apparatus for urinary elimination as claimed in claim 1 comprises:
    the absorbency fragrance materials and the liquid absorbency materials being adjacently positioned with the bottom wall and the lateral wall;
    the hydrophilic layer being perimetrically connected to the lateral wall;
    the hydrophilic layer being positioned in between the bottom wall and the outer lip; and
    the hydrophilic layer being positioned atop the absorbency fragrance materials and the liquid absorbency materials.

4. The portable and disposable apparatus for urinary elimination as claimed in claim 1 comprises:
    the top face and the bottom face being oppositely positioned from each other on the lid;
    the sealed section and the resealable section being adjacently positioned with each other on the lid;
    the adhesive strip being perimetrically positioned around the resealable section;
    the adhesive strip being adjacently positioned with the bottom face;

the removable film being perimetrically attached around the adhesive strip opposite from the bottom face; and the tab being connected to the resealable section opposite from the sealed section.

5. The portable and disposable apparatus for urinary elimination as claimed in claim 1 comprises:

the at least one pack of wipe being attached on to the container.

6. The portable and disposable apparatus for urinary elimination as claimed in claim 5 comprises:

the at least one pack of wipe comprises a cleaning wipe and a wrapper; and the cleaning wipe being enclosed by the wrapper.

7. A portable and disposable apparatus for urinary elimination comprises:

a container;
a hydrophilic layer;
absorbent fragrance materials;
liquid absorbency materials;
a lid;
at least one pack of wipe;
the container comprises an outer lip, a bottom wall, and a lateral wall;
the lid comprises a top face, a bottom face, a sealed section, a resealable section, an adhesive strip, a removable film, and a tab;
the top face and the bottom face being oppositely positioned from each other on the lid;
the sealed section and the resealable section being adjacently positioned with each other on the lid;
the adhesive strip being perimetrically connected around the resealable section;
the adhesive strip being adjacently positioned with the bottom face;
the removable film being perimetrically attached around the adhesive strip opposite from the bottom face;
the tab being connected to the resealable section opposite from the sealed section;
the hydrophilic layer, the absorbency fragrance materials, the liquid absorbency materials being positioned within the container; and
the lid being positioned atop the container.

8. The portable and disposable apparatus for urinary elimination as claimed in claim 7 comprises:

the lateral wall being perimetrically positioned around the bottom wall;
the lateral wall being extended above the bottom wall;
the outer lip being perimetrically positioned around the lateral wall; and
the outer lip being positioned parallel with the bottom wall and extended away from the bottom wall.

9. The portable and disposable apparatus for urinary elimination as claimed in claim 7 comprises:

the absorbency fragrance materials and the liquid absorbency materials being adjacently positioned with the bottom wall and the lateral wall;
the hydrophilic layer being perimetrically connected to the lateral wall;
the hydrophilic layer being positioned in between the bottom wall and the outer lip; and
the hydrophilic layer being positioned atop the absorbency fragrance materials and the liquid absorbency materials.

10. The portable and disposable apparatus for urinary elimination as claimed in claim 7 comprises:

the top face and the bottom face being oppositely positioned from each other on the lid;
the sealed section and the resealable section being adjacently positioned with each other on the lid;
the adhesive strip being perimetrically connected around the resealable section;
the adhesive strip being adjacently positioned with the bottom face;
the removable film being perimetrically attached around the adhesive strip opposite from the bottom face; and
the tab being connected to the resealable section opposite from the sealed section.

11. The portable and disposable apparatus for urinary elimination as claimed in claim 7 comprises:

the sealed section being permanently connected with the outer lip;
the resealable section being attached with the outer lip through the removable film; and
the removable film being positioned in between the adhesive strip and the outer lip.

12. The portable and disposable apparatus for urinary elimination as claimed in claim 7 comprises:

the at least one pack of wipe being attached on to the container.

13. The portable and disposable apparatus for urinary elimination as claimed in claim 12 comprises:

the at least one pack of wipe comprises a cleaning wipe and a wrapper; and
the cleaning wipe being enclosed by the wrapper.

14. A method of using the portable and disposable apparatus for urinary elimination comprises the steps of:

providing a portable and disposable apparatus for urinary elimination, wherein the portable and disposable apparatus for urinary elimination comprises a container, a lid which is positioned atop the container, and at least one pack of wipe which is positioned on the container;
completely opening a resealable section of the lid from the container, wherein the inside of the container is exposed;
lifting the resealable section and placing the container under a urethral opening for urine discharge;
urinating into the container and holding the resealable section in front of the urethral opening;
removing the at least one pack of wipe from the container, wherein the at least one pack of wipe comprises a cleaning wipe and a wrapper;
opening the wrapper and removing the cleaning wipe;
cleaning the urethral opening with the cleaning wipe;
placing the cleaning wipe and the wrapper inside the container;
removing a removable film from the resealable section in order to expose an adhesive strip;
placing the removable film inside the container;
sealing the resealable section onto the container through the adhesive strip; and
disposing the container.

15. The method of using the portable and disposable apparatus for urinary elimination as claimed in claim 14 comprises:

wherein the resealable section functions as a privacy shield to the urethral opening.

16. The method of using the portable and disposable apparatus for urinary elimination as claimed in claim 14 comprises:

wherein the resealable section functions as a splash guard to the container.

17. The method of using the portable and disposable apparatus for urinary elimination as claimed in claim 14 comprises:

wherein absorbent fragrance materials and liquid absorbency materials solidify the urine.

\* \* \* \* \*